(12) United States Patent
Yamaguchi

(10) Patent No.: US 7,718,123 B2
(45) Date of Patent: May 18, 2010

(54) EXTENDED LIFE MINERAL ACID DETECTION TAPE

(75) Inventor: Tamami Yamaguchi, Lake Forrest, IL (US)

(73) Assignee: Honeywell Analytics AG, Uster (CH)

( * ) Notice: Subject to any disclaimer, the term of this patent is extended or adjusted under 35 U.S.C. 154(b) by 1183 days.

(21) Appl. No.: 11/210,125

(22) Filed: Aug. 23, 2005

(65) Prior Publication Data
US 2006/0073071 A1    Apr. 6, 2006

Related U.S. Application Data

(60) Provisional application No. 60/604,945, filed on Aug. 27, 2004.

(51) Int. Cl.
G01N 21/00 (2006.01)
G01N 33/00 (2006.01)
G01N 21/77 (2006.01)

(52) U.S. Cl. .......................... 422/56; 422/57; 436/111; 436/164; 436/169

(58) Field of Classification Search .................. 422/56, 422/57; 436/111, 164, 169
See application file for complete search history.

(56) References Cited

U.S. PATENT DOCUMENTS

| | | | | |
|---|---|---|---|---|
| 2,440,526 A | * | 4/1948 | Soloman | 205/53 |
| 3,585,001 A | | 6/1971 | Mast | |
| 3,817,705 A | | 6/1974 | Stein et al. | |
| 3,838,972 A | * | 10/1974 | Richards et al. | 436/100 |
| 4,174,292 A | * | 11/1979 | Seidenberger et al. | 510/100 |
| 4,190,419 A | * | 2/1980 | Bauer | 436/97 |
| 4,420,567 A | | 12/1983 | McMahon et al. | |
| 4,434,235 A | * | 2/1984 | Rabi et al. | 436/110 |
| 5,250,441 A | | 10/1993 | Vogt et al. | |
| 5,397,536 A | | 3/1995 | Nakano et al. | |
| 5,624,546 A | * | 4/1997 | Milco | 205/779.5 |
| 6,096,557 A | | 8/2000 | Tanaka et al. | |
| 6,217,827 B1 | | 4/2001 | Zhang et al. | |
| 2003/0175984 A1 | | 9/2003 | Fukuoka et al. | |

FOREIGN PATENT DOCUMENTS

| | | | |
|---|---|---|---|
| JP | 07-072138 | | 3/1995 |
| WO | WO02/079746 A1 | * | 10/2002 |
| WO | WO2006038028 A1 | * | 4/2006 |

OTHER PUBLICATIONS

Nakano et al., Development of a Monitoring Tape for Hydrogen Chloride Gas Using Metanil Yellow, 1993, Analyst, vol. 118, p. 1539-1542.*

Nagashima et al., Improvement of a monitoring tape for nitrogen dioxide in air, 1999, Elsevier Science, vol. 49, p. 305-308.*

(Continued)

*Primary Examiner*—Lori Jarrett
(74) *Attorney, Agent, or Firm*—Husch Blackwell Sanders Welsh & Katz

(57) ABSTRACT

A mineral acid detection tape includes a cellulose paper substrate saturated with a formula solution and provides an extended life detection tape of at least a three-month period of time when place in service.

7 Claims, 5 Drawing Sheets

OTHER PUBLICATIONS

Nakano et al., Development of a monitoring system for vinyl chloride gas in air by using an HCI monitoring tape and pyrolyzer, 1996, Elsevier Science, Talanta 43, p. 459-463.*

West et al., The Determination of Sulfuric Acid Aerosols, 1974, Analytica Chimica Acta, 69, p. 111-116.*

European Search Report Communication—Dated Oct. 4, 2006—reference Case 103—regarding Application No./Patent No. 05255286.6-2204—Applicant/Proprietor: Zellweger Analytics AG, re: listing of documents cited in the European search report—(3 pages).

* cited by examiner

EXTENDED LIFE MINERAL ACID DETECTION TAPE

CROSS-REFERENCE TO RELATED APPLICATION

This application is related to and claims the benefit of U.S. Provisional Application Ser. No. 60/604,945 filed Aug. 27, 2004, the teachings of which are incorporated herein by reference.

BACKGROUND OF THE INVENTION

The present invention relates to an extended life mineral acid detection tape and, in particular, to a mineral acid detection tape which possesses uniform gas sensitivity and acceptable background color for at least a three-month time period when placed in usage.

DESCRIPTION OF THE PRIOR ART

At present, existing mineral acid detection tapes are available based upon several types of chemistry. One acid detection system utilizes a mineral acid detection tape containing a pH indicator dye. However, the acid based stains on the detector tape are not stable and the pH indicator dyes themselves are toxic. Also in such a system, the relationship between the acid gas concentration and the stain color intensity is non-linear thereby requiring the need of complex optical monitor assemblies. Moreover, a limited number of pH indicating dyes are available for use with such optical monitor assemblies and such detection tapes have a limited useful life of approximately a one-month time period.

Another mineral acid detector tape system relies upon a diazo-coupling reaction in an acid phase to provide an intense red color indicative of the presence of acid gases. Although such a system is sensitive to acid gases, such a system has a limited useful lifetime. Also, the sensitivity and tape background colors of such a system are unstable to chemicals, such as primary amines and coupling reagents in the tape formula which possess temperature and light sensitivities. Over time, the background of such mineral acid gas detection tape darkens, and as the tape background darkens, the sensitivity of the tape decreases. For example, such tapes exhibit significant background drops within a 4-6 week period of use. Also, under room temperature conditions, such tape darkening results in a 30-40% optic reading drop within a 30-day period. Additionally, such detection systems possess unstable tape sensitivities and reduction in sensitivity of between 10-20% within a 30-day period and between 40-60% within a 90-day period. Accordingly, the useful life of such mineral acid detection tape systems are limited to at most a 30-day period of time after they are placed in service. Thus, such tapes must be replaced after a 30-day period of use to provide acceptable monitoring of acid gases.

Also, the reaction rate between the acid gas concentration and the tape color intensity is non-linear at low concentrations of acid/gas detections. The resultant reaction curves are S-shaped, which result in a slow response and a narrow detection range for such mineral acid detection tapes.

SUMMARY OF THE INVENTION

One object of the present invention is to provide a solution to the limited lifetime of existing mineral acid detection tapes. This solution is achieved by utilizing diazo-coupling reagents possessing low toxicity and reduced dependency on temperature and light to thereby provide an improved mineral acid detection tape possessing a useful life of at least 3 months.

It is an object of the present invention to provide a mineral acid detection tape which possesses a uniform tape background stability under room temperature conditions over an extended period of time of at least 90 days.

Still another object of the present invention is to provide a mineral acid detector tape that is sensitive to low acid concentration levels over an extended period of time.

Yet another object of the present invention is to provide diazo-coupling reagents possessing low toxicity resistance and reduced dependency to temperature and light within a stable gas detection tape over an extended period of time.

Still a further object of the present invention is to provide an alkalized mineral acid detection tape which is stable over an extended pH range.

It is another object of the present invention to use a polyalcohol to uniformly impregnate an acid detector tape with diazo coupling reagents to provide a tape possessing moisture and sample gas trapping efficiency for at least 90 days.

In accordance with the present invention, an acid gas detection tape for detecting mineral acid gases, such as hydrochloric acid, hydrobromic acid, hydrofluoric acid, hydriodic acid, nitric acid, sulphuric acid, phosphoric acid, and acetic acid, is provided and which extends the useful life of the mineral acid detecting paper up to at least a three-month period of time when placed in usage.

The extended life mineral acid detection tape is saturated with a formula solution by passing the cellulose paper substrate through a bath containing the formula solution. The formula solution includes a pH buffer of between 8-9% by volume of the total volume of solvent and between about 0.07-0.10% by weight of the total weight of solvent of reagent grade chromotropic acid is added to the composition as a coupling agent. Sodium nitrate, within the composition range of 0.25-0.38% by weight of the total weight of solvent, is added to the formula composition to facilitate the diazotization reaction. A stabilizer of sodium bromide of between 0.3-0.5% by weight of the total weight of the solvent is added to the composition and a diazotization coupling agent, reagent grade sulphanilic acid, of between a weight percent of 0.15-0.35% by the total weight of the solvent is added to the composition. A pH indicator, containing 0.1% ethyl red, of between 4-4.5% by volume of the total volume of solvent is added to the composition, and a humectant comprised of a polyalcohol of between 4-5.5% by volume of the total volume of solvent is added to the composition. Each of the reagents is dissolved in the order shown in an amount of between 3.3 to 3.5 liters of methyl alcohol as the solvent.

When the formula solution is properly mixed, a paper tape substrate is then passed through a bath containing the formula solution. The coated paper substrate is then passed through a oven, one meter in length, that is maintained within a temperature range of 70-80° C. The coated tape paper travels at a speed of between 2.2 to 3.4 meters per minute through the oven. The dried mineral acid detection tape exiting the drying oven possesses a light or faint yellow tinge of color.

DESCRIPTION OF THE PREFERRED EMBODIMENT

Figure 1:
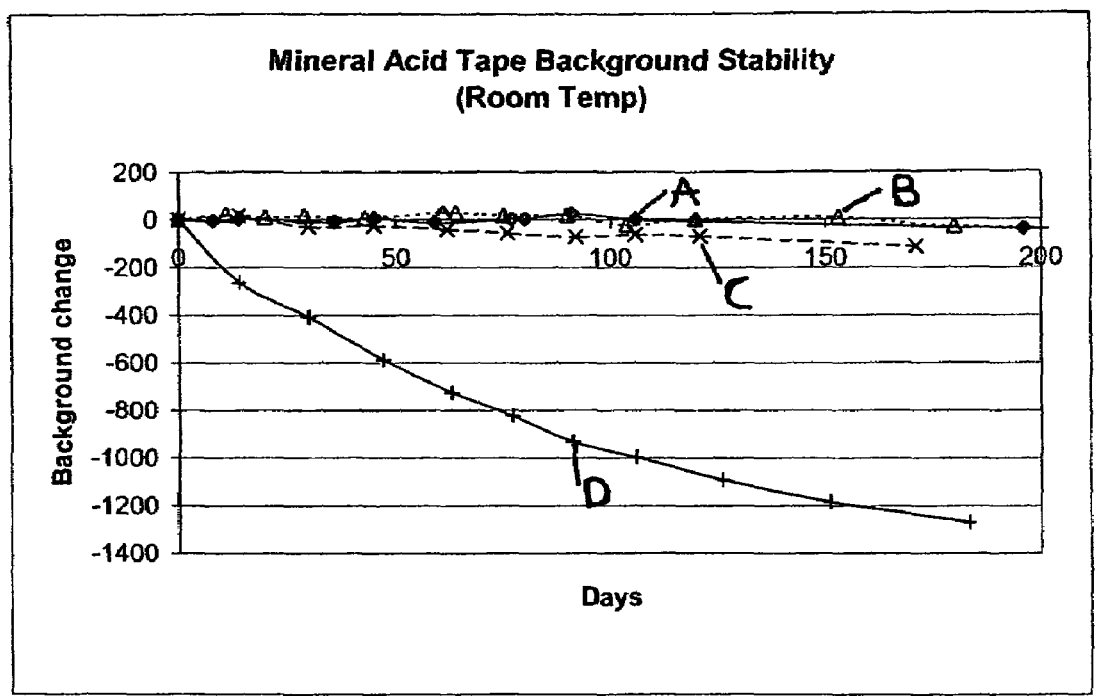
FIG. 1 is a graph of the background stability of extended life mineral acid detection tapes in accordance with the present invention under room temperature conditions as compared to the background stability of a conventional mineral acid detection tape.

The present invention relates to a extended life mineral acid detection tape for monitoring the presence of mineral acids in the environment. A cellulose tape paper substrate (identified as Chroma-1 from Whatman, Inc.) is saturated with the formula solution in accordance with the present invention to provide a detection tape that possesses an extended life of at least 90 days.

The formula solution is comprised of a pH buffer of 0.26 M sodium hydroxide plus 0.009 M of Borax, which is 8-9% by volume of the total volume of a solvent. In the alternative, the pH buffer may be 0.28 M sodium hydroxide plus 0.15 M of 3-(cyclohexylamino)-1-propanesulfonic acid (hereinafter referred to as CAPS), which is 8-9% by volume of the total volume of the solvent. By reducing the amount of the pH buffer, the tape sensitivity is increased while the background darkening is increased. Increasing the amount of the buffer solution above this range results in the sensitivity of the formula solution being lowered. The pH buffer material and the glycol propoxylate humectant are utilized for stabilization of the detection tape.

A coupling agent of reagent grade chromotropic acid of between 0.07-0.1% by weight of the total weight of the solvent is added to the formula solution. By increasing the amount of this coupling agent to the formula, the background darkening of the tape background is accelerated due to the excess amount of coupling agent, which causes self-coupling of the coupling agent.

The formula solution may optionally contain a reagent grade N-naphthylethylenediamine dihydrochloride (hereinafter referred to as NED) of about 0.05-0.11% by weight of the total weight of the solvent. The NED is used to increase the sensitivity to hydrochloric acid gas. The background darkening is accelerated faster due to the excess amount of coupling agent, which causes self-coupling of the reaction mechanism. The optional coupling agent NED may also be selected from the group of N,N Dimethylaniline, iminodibenzyl, and gentistic acid. The formula solution further includes a sodium nitrite for the diazotization reaction. The amount of sodium nitrite is between 0.25-0.38% by weight of the total weight of solvent.

Also, the formula utilizes a stabilizer comprised of sodium bromide. The amount of stabilizer is between 0.032-0.05% by weight of the total weight of the solvent.

The formula solution further includes reagent grade sulphanilic acid as a diazotization coupling agent. The amount of the coupling agent is between 0.15-0.35% by weight of the total weight of the solvent. The coupling agent may also be selected from the group of metanilic acid, anthranilic acid, m-aminoacetoanilide and p-nitroaniline. The formula solution additionally includes a pH indicator, containing 0.1% ethyl red, of between 4-4.5% by volume of the total volume of the solvent. The pH indicator is red at approximately a pH of 4.5 and is yellow at a pH of 6.5. By increasing the amount of the pH indicator, the linearity at the beginning of detection is enhanced. It is desired that color change occur from colorless/yellow to red or blue when contacted with the acid gas. Additional indicators acceptable for use in the formula solution may be selected from the group of ethyl orange, methyl red and metanil yellow.

Finally, a humectant, which is a polyalcohol comprised of one part ethylene glycol and one part glycerol propoxylate, of between 4-5.5% by volume of the total volume of solvent, is added to the formula solution. By decreasing the amount of glycerol propoxylate in the polyalcohol, the sensitivity of the detection tape is increased upon exposure to the target gas. However, the darkening of the tape background occurs more rapidly. By increasing the amount of this humectant material, the sensitivity is lowered. Other humectants that may be utilized are polyethylene glycol or glycerol.

Each of the reagents, including the pH buffer and the coupling agent, the nitrite for diazotization, the stabilizer, the diazotization coupling agent, the pH indicator and the humectant are dissolved in the order described in 3.3-3.5 liters of methyl alcohol as the solvent. Although ethyl alcohol may be used as the solvent, this solvent results in lower sensitivity and lower gas trapping efficiency.

The nitrite ions present in the formula solution and the aromatic amine react with an acid gas present in a sample gas stream to form an intermediate diazonium salt, as shown by (1). This diazonium salt is characterized by containing diazonium ions, which are electrophiles that seek out species of electrons which can be shared to reach equilibrium.

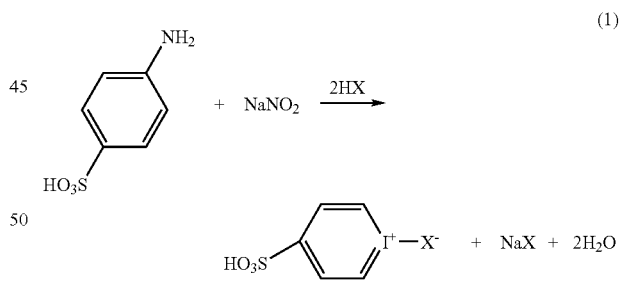

(1)

The diazonium salt couples with the aromatic coupling compound, the chromotropic acid, to form the red-orange colored azo complexes, as shown by (2).

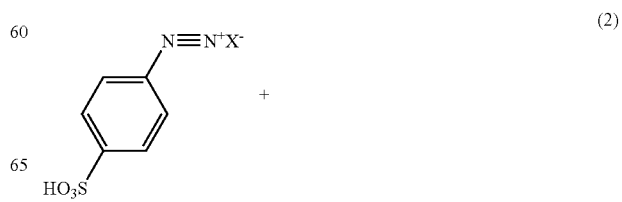

(2)

-continued

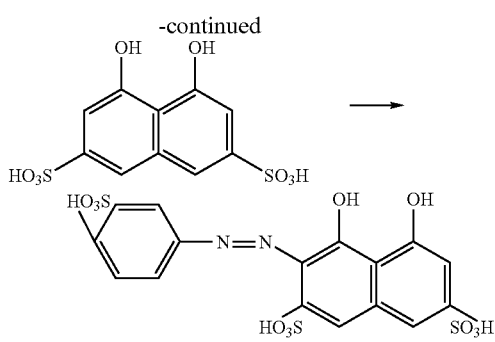

These complexes are evident as a visible color stain on the saturated and extended life mineral acid detection tape. The intensity of the color stain on the tape relates to the amount of the toxic gas present in the sample stream.

The mineral acids that can be detected utilizing this acid detection tape include hydrogen bromide, hydrogen chloride, hydrogen fluoride, hydrogen iodide, nitric acid, sulphuric acid, phosphoric acid, and acetic acid.

The detection tape is comprised of a cellulose paper substrate, which is commercially available as Chroma-1. The paper detection tape is saturated with the formula solution by passing the paper tape through a bath containing the formula solution. The tape is then passed through an oven having a length of approximately one meter and which is maintained between 70-80° C. The saturated tape is advanced through the oven at a speed to provide a residence time within the oven of between about 45 to 75 seconds. Upon exiting the oven, the tape has a light yellow color and is wound onto the cassette.

As shown in FIGS. 1-5, the paper detection tape is saturated with variations of the formula solution to provide various samples A-C which are compared with a sample detection tape D in accordance with the prior art. In FIGS. 1-5, Sample A is the standard formula solution utilizing the pH buffer containing borax and the polyalcohol of one part ethylene glycol and one part gylcerol propoxylate, Sample B is the standard formula solution of Sample A wherein the pH buffer contains 10% less glycerol propoxylate, Sample C is the standard formula solution of Sample A wherein the pH buffer includes 3-(cyclohexylamino)-1-propanesulfonic acid (CAPS), and Sample D is a paper detection tape representative of the prior art which contains p-nitroaniline, an aromatic amine, which reacts to provide the diazonium salt which in turn reacts with the coupling compound N-naphthylethylene dihydrocloride.

Figure 2:
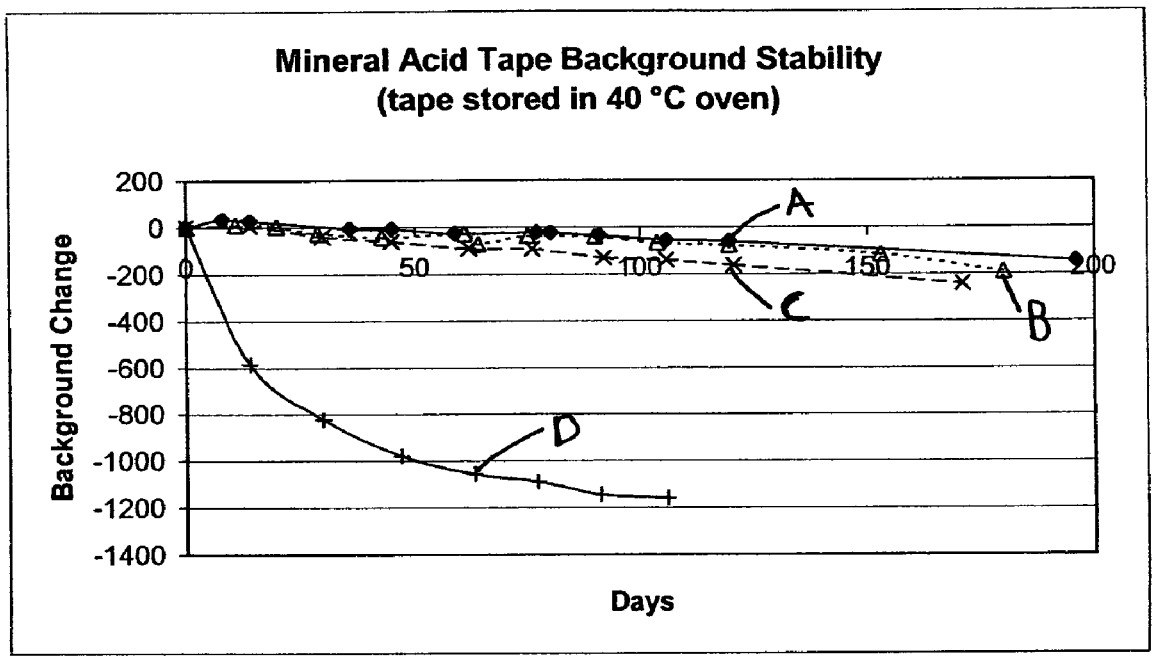
FIG. 2 is graph of the tape sensitivity stability of extended life mineral acid detection tapes in accordance with the present invention under elevated temperature conditions as compared to the background stability of a conventional mineral acid detection tape.
Figure 3:
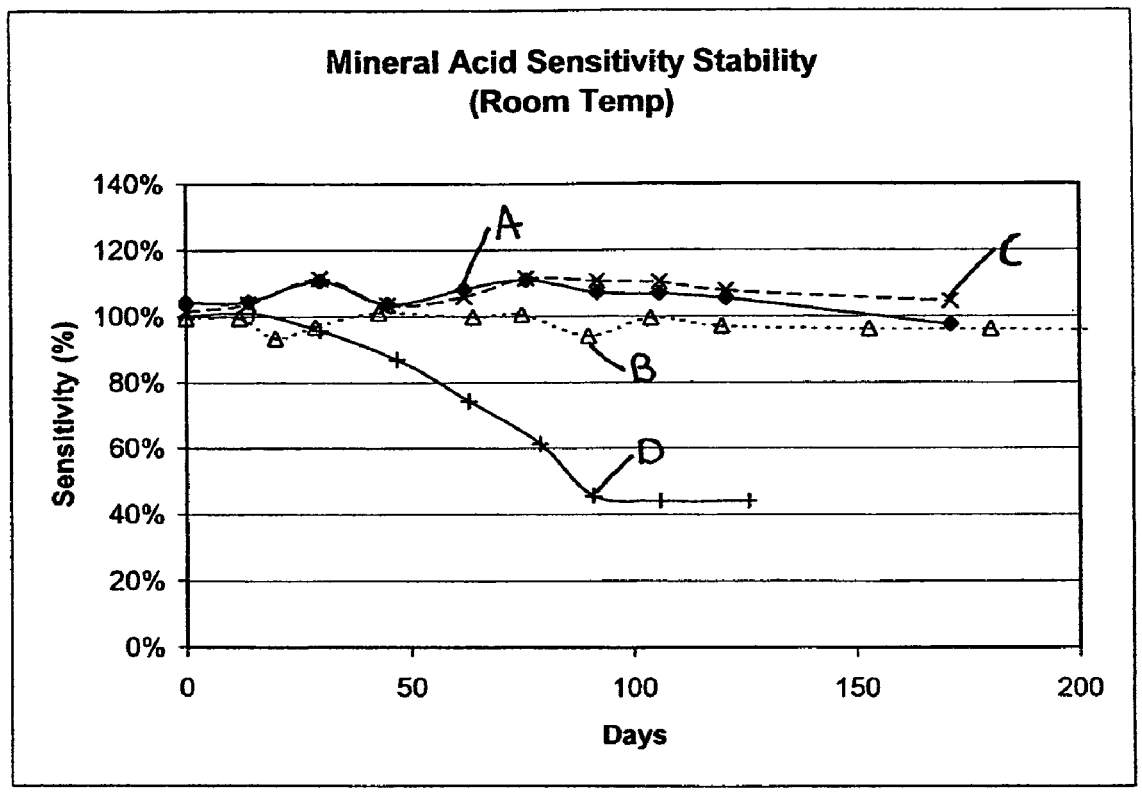
FIG. 3 is a graph of the sensitivity stability of extended life mineral acid detection tapes in accordance with the present invention under room temperature conditions as compared to the sensitivity stability of a conventional mineral acid detection tape.
Figure 4:
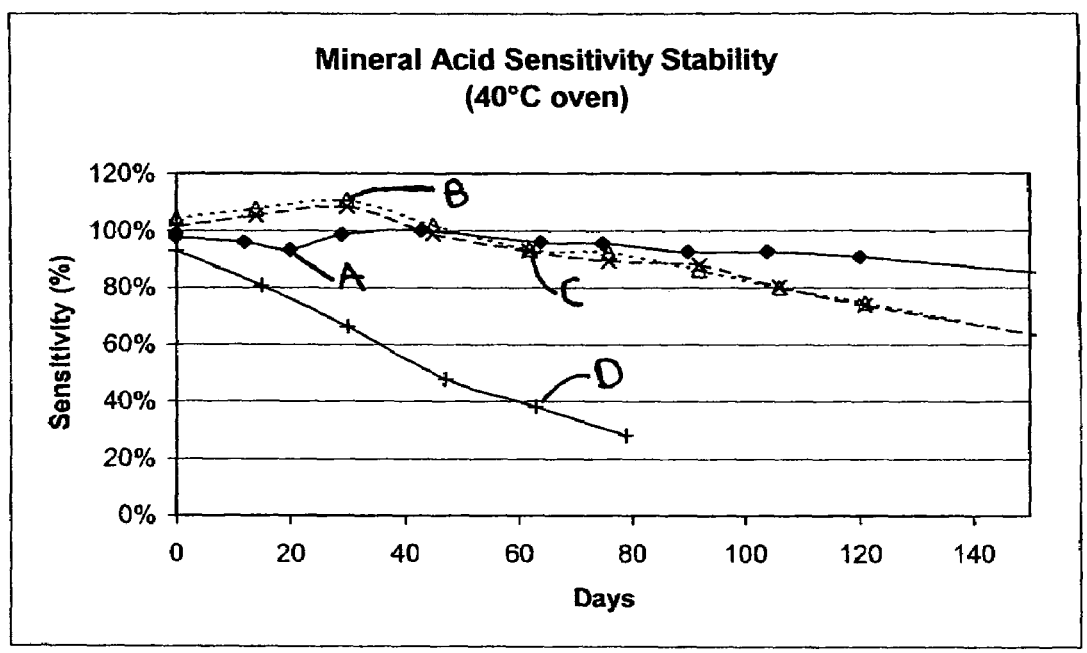
FIG. 4 is a graph of the sensitivity stability of extended life mineral acid detection tapes in accordance with the present invention under elevated temperature conditions as compared to the sensitivity stability of a conventional mineral acid detection tape.

Specifically, in FIGS. 1 and 2, the paper detection tapes, Samples A-C, are treated with the formula solution and provide a stable background well in excess of 90 days. Specifically, in FIG. 1 the background changes within 100 optics, a 5% drop within 90 days, under room temperature conditions, and within 100-300 optics reading a 10% drop under high temperature conditions, as shown in FIG. 2. Also, as shown in FIGS. 3 and 4, the paper detection tapes, Samples A-C, are treated with the formula solution under room temperature (FIG. 3) and high temperature (FIG. 4) and provide a sensitivity of within ±10% over at least 90 days while the conventional acid detecting tape, represented by Sample D, results in a sensitivity drop of between about 40-60%.

Figure 5:
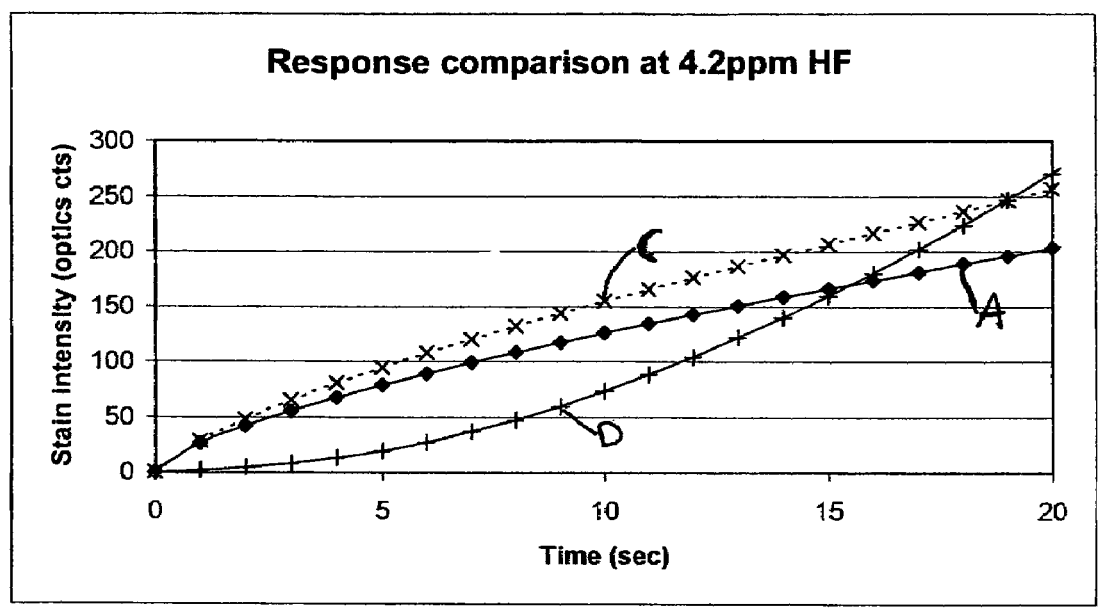
FIG. 5 is a graph of the response time at a low end gas concentration of an extended mineral acid detection tapes in accordance with the present invention as compared to the response time of a conventional mineral acid detection tape.

Additionally, as shown in FIG. 5, the paper detection tapes, Samples A and C, treated with the formula solution provides increased response times for low acid gas concentration levels when compared to an existing acid detection tape, Sample D.

Illustrated and described above is regarded to be the preferred embodiment of the present invention, nevertheless it will be understood that such are merely exemplary and that numerous modifications and rearrangement may be made herein without departing from the spirit of the invention.

The invention claimed is:

1. A detector tape for detecting mineral acids in an air stream comprising: a substrate impregnated with a formula solution consisting essentially of (a) a pH buffer material at a concentration of between about 8-9% by volume of the total volume of solvent, (b) a first coupling agent consisting of reagent grade chromotropic acid of between 0.07-0.10% by weight of the total weight of the solvent, (c) sodium nitrite reacting with the acid gas and a diazotization coupling agent to form the diazonium salt, said sodium nitrite having a concentration of between 0.25-0.38% by weight of the total weight of the solvent, (d) a sodium bromide stabilizer of between about 0.30-0.050% by weight of the total weight of the solvent, (e) said diazotization coupling agent of between about 0.15-0.35% by weight of the total weight of solvent, (f) a pH indicator of between 4-4.5% by volume of the total volume of solvent and (g) a humectant comprised of a polyalcohol of between 4-5.5% by weight of the total volume of solvent, with each element of the formula solution being dissolved in between 3.3 to 3.5 liters of methanol solvent.

2. The detector tape consisting of the formula solution in accordance with claim 1, wherein said pH buffer material is selected from a group consisting essentially of 0.26 M sodium hydroxide and 0.009 M sodium borate or 0.028 M sodium hydroxide and 0.15 M 3-(cyclohexylamino)-1-propanesulfonic acid or 0.26 M sodium hydroxide and 0.012 M sodium bicarbonate.

3. The detector tape consisting of the formula solution in accordance with claim 1, wherein said diazotization coupling agent is selected from a group consisting essentially of reagent grade sulfanilic acid, metanilic acid, anthranilic acid, m-amino acetanilide and p-nitroaniline.

4. The detector tape consisting of the formula solution in accordance with claim 1, wherein said pH indicator is selected from a group consisting essentially of ethyl red, ethyl orange, methyl red and metanil yellow.

5. The detector tape consisting of the formula solution in accordance with claim 1, wherein said humectant is selected from a group consisting essentially of one-part ethylene glycol plus one-part glycerol propoxylate or polyethylene glycol or glycerol.

6. The detector tape consisting of the formula solution in accordance with claim 1, wherein said formula solution further includes a second coupling agent added to the formula solution after the addition of said sodium bromide stabilizer.

7. The detector tape consisting of the formula solution in accordance with claim 6, wherein said second coupling agent is selected from a group consisting essentially of reagent grade N-(1-naphyl)ethylenediamine dihydrochloride, N,N-dimethylaniline, iminodibenzyl and gentisic acid.

* * * * *